United States Patent [19]
Bannerjee et al.

[11] Patent Number: 5,912,737
[45] Date of Patent: Jun. 15, 1999

[54] SYSTEM FOR VERIFYING THE CALIBRATION OF A TURBIDIMETER

[75] Inventors: Ashim K. Bannerjee, Westminster; Robert D. Stream, Loveland, both of Colo.

[73] Assignee: Hach Company, Loveland, Colo.

[21] Appl. No.: 09/088,333

[22] Filed: Jun. 1, 1998

[51] Int. Cl.$^6$ .............................. G01N 21/00; G01J 1/02
[52] U.S. Cl. .................. 356/364; 356/243.2; 356/338
[58] Field of Search ................ 356/335–343, 356/364–369, 432–442, 243.2; 250/573–576

[56] References Cited

U.S. PATENT DOCUMENTS

| | | | |
|---|---|---|---|
| 3,177,761 | 4/1965 | Redner | 356/366 |
| 3,627,431 | 12/1971 | Komarniski | 356/441 |
| 3,653,767 | 4/1972 | Liskowitz | 356/366 |
| 3,790,289 | 2/1974 | Schmidt | 356/434 |
| 3,918,817 | 11/1975 | Posgate | 356/442 |
| 5,250,186 | 10/1993 | Dollinger et al. | 356/366 |

*Primary Examiner*—Hoa Q. Pham
*Attorney, Agent, or Firm*—Dean P. Edmundson

[57] ABSTRACT

A system is described for verifying the calibration of a turbidimeter having a light source and a detector for scattered light. A first polarizer is positioned in the path of the light beam, and a second polarizer is positioned between the first polarizer and the detector. The first polarizer linearly polarizes the light beam and the second polarizer restricts the amount of light passing through it to reach the detector.

6 Claims, 2 Drawing Sheets

SYSTEM FOR VERIFYING THE CALIBRATION OF A TURBIDIMETER

FIELD OF THE INVENTION

This invention relates to turbidimeters and calibration verification systems. More particularly, this invention relates to systems for verifying whether a turbidimeter is properly calibrated.

BACKGROUND OF THE INVENTION

Turbidimeters are well-known instruments which are used to determine the extent of turbidity in liquids (particularly water) and normally report the turbidity in terms of NTU (Nephelometric Turbidity Units). Turbidimeters determine turbidity of a liquid by measuring the extent of light scattering of a light beam projected through the liquid in a cell. Light is scattered by particles present in the liquid. Greater numbers of particles in the liquid result in greater turbidity values.

Periodically it is necessary to verify that a turbidimeter is properly calibrated. One manner of doing this is to prepare a series of standard liquid compositions of known turbidity and then taking turbidity measurements of each standard composition. By comparing the instrument reading with the known turbidity value of each standard composition, it is possible to verify whether the instrument is properly calibrated. However, this is a very time-consuming, tedious and expensive procedure.

A commercially available device which has been used for verifying the calibration of a turbidimeter is a solid glass cube which has been doped with a material having a refractive index slightly different from that of the glass itself. When a light beam in the turbidimeter passes through the glass cube it is scattered by the dopant material. The scattered light forms a signal at the detector in the instrument. There are a number of disadvantages associated with the use of this technique, including: (a) the turbidimeter must be dried and cleaned before the cube can be inserted, (b) the cost of the cube is very significant, and (c) it is not possible to manufacture cubes which provide exactly the same light scattering value (consequently each cube must be individually certified by the manufacturer).

There has not heretofore been provided a calibration verification system having the features and advantages provided by the present invention.

SUMMARY OF THE INVENTION

In accordance with the present invention there is provided a system for verifying the calibration of a turbidimeter which avoids the problems and disadvantages associated with the previously-known methods and systems.

In a preferred embodiment the system of the invention comprises a reflection device which includes a mechanism for tuning the amount of light seen by the light sensor or detector in the turbidimeter. The mechanism includes two polarizer film means which are located in the optical path of the light beam in the turbidimeter. The first polarizer means renders the light beam linearly polarized. The second polarizer means can then be rotated so as to restrict the amount of light passing through it. This enables the system to be tuned to the desired NTU reading.

The calibration verification device or system can be set at the time of manufacture to provide a given value of turbidity (e.g., 0.5, 1.0, 20.0 NTU etc.). The reading set by the manufacturer for a particular device will remain stable over time with minimal influence from minor temperature variations, humidity fluctuations and mechanical vibration.

The device or system of the invention can be easily attached to the turbidimeter head to form a light-tight measurement cavity. This eliminates the need for a separate calibration cylinder (as is required when using standard liquid compositions), or for draining and drying the turbidimeter and then restarting the flow for sample measurement.

Other features and advantages of the system of the invention will be apparent from the following detailed description and accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
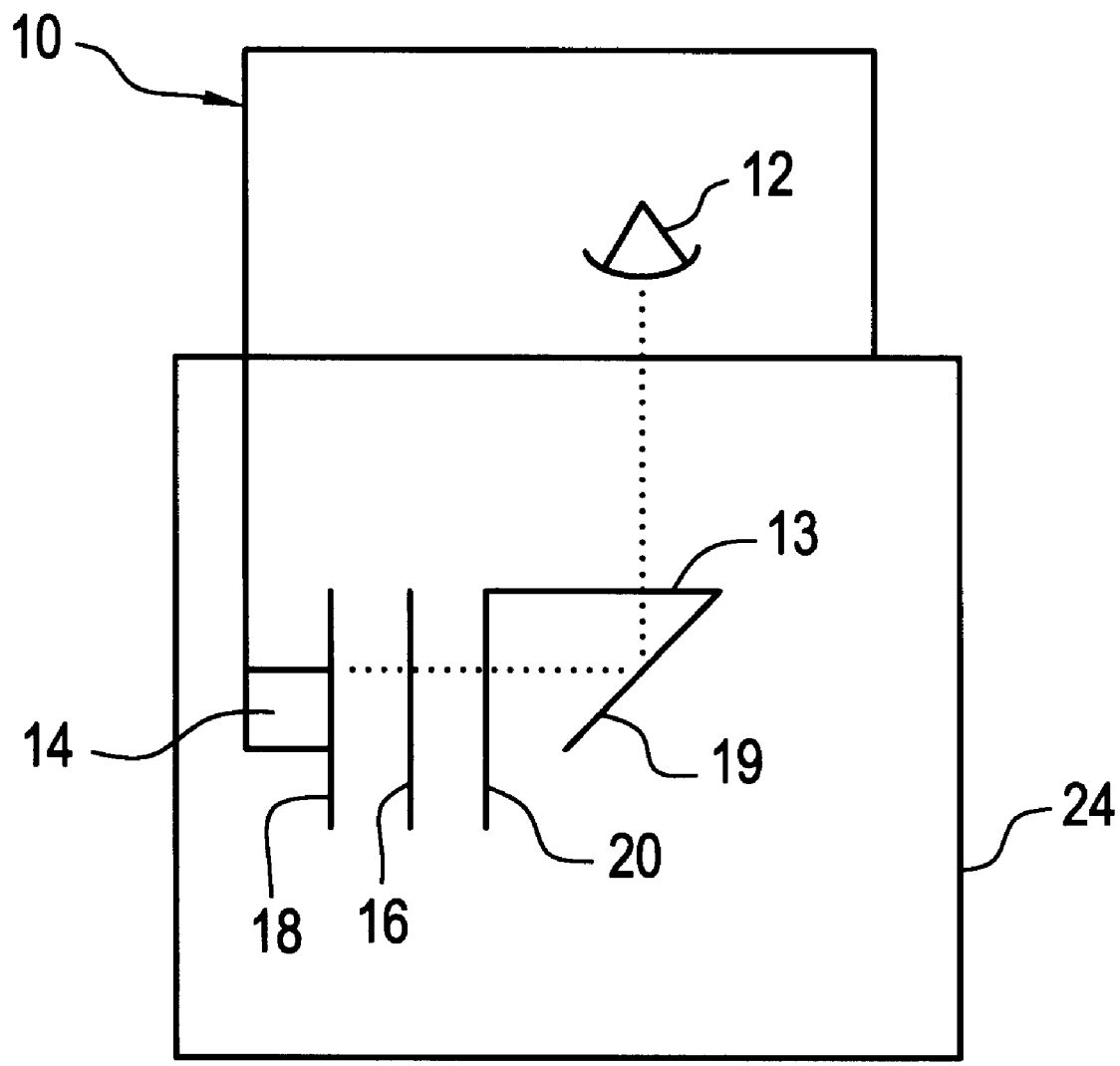
FIG. 1 is a schematic diagram of the system of this invention connected to a turbidimeter head.

In the drawings there is shown a conventional turbidimeter head 10. The turbidimeter includes a light source 12 and a light detector 14. First and second polarizer means 16 and 18 are positioned in the path of the light beam.

The first polarizer renders the random polarization of the incident beam to a linearly polarized beam. The second polarizer is positioned in the path of the radiation passing through the first polarizer and controls the intensity of the radiation which is able to pass therethrough.

By rotating the second polarizer, it is possible to tune the system such that a predetermined amount or intensity of light is able to pass through it to reach the detector. For example, when the device is manufactured, it is possible to rotate the second polarizer and then secure it in a fixed position such that a predetermined amount of light passes through it (e.g., 0.5, 1.0, 20.0 NTU etc.). This device is then useful as a calibration verification device for a turbidimeter.

Figure 2:
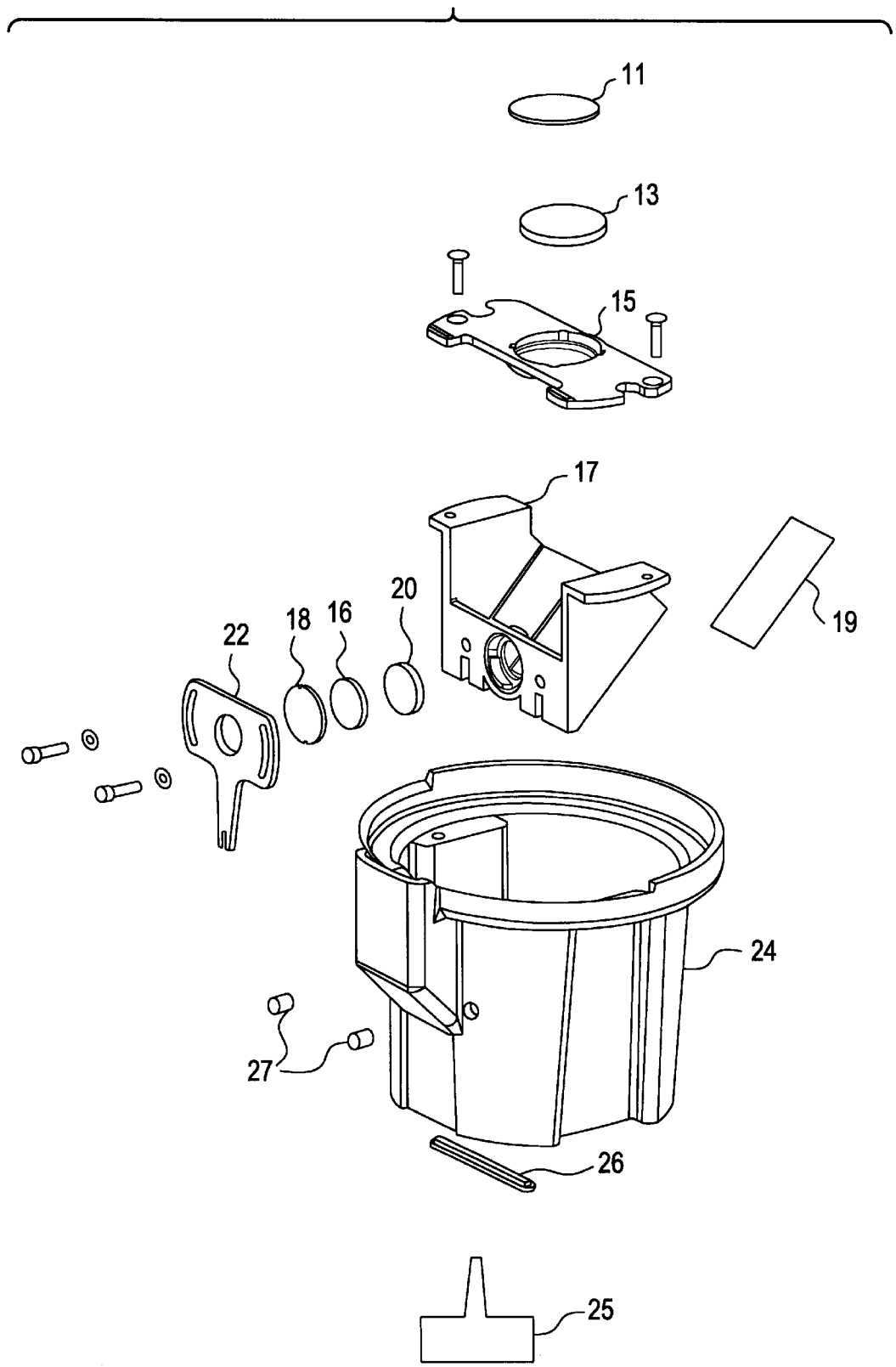
FIG. 2 is an explosion view showing a turbidimeter and a calibration verification device of the invention.

FIG. 2 is an exploded view showing the various components included a preferred embodiment of calibration verification device for use with a turbidimeter. The system includes a light shaping diffuser 11 (for homogenizing the incident light beam from the light source), infrared filter or mirror 13 (for blocking out radiation above about 700 nm), filter mount 15, beam splitter and filter mount 17, beam splitter 19, infrared filter or mirror 20, polarizer means 16 (for rendering incident radiation from the light source linearly polarized), polarizer means 18 parallel to the first polarizer for controlling the intensity of the radiation passing through it, and a rotatable mount 22 for polarizer 18. An enclosure 24 may be provided for enclosing the system in a light-tight environment. A tool 25 may also be provided for rotating polarizer 18, and plugs 26 and 27 may be used for blocking access to the rotatable mount for polarizer 18.

Other variants of the system are also possible. For example, a light source may be used which emits essentially only near infrared radiation (as opposed to visible light). In such case, there is no need or desire to include the infrared filters shown in the drawings, and the polarizers would be replaced with commercially available near infrared polarizer means.

Other variants are also possible without departing from the scope of this invention.

What is claimed is:

1. A system for verifying the calibration of a turbidimeter of the type including a light source emitting a light beam and a detector for detecting scattered light, the system comprising:

(a) a first polarizer means positioned in the path of said light beam; and (b) second polarizer means positioned in the path of said light beam between said first polarizer means and said detector; wherein said second polarizer means is positioned such that a predetermined amount of said light beam passes therethrough to said detector;

wherein said first polarizer means is capable of linearly polarizing said light beam, and wherein said second polarizer means is capable of restricting the amount of light passing through it to reach said detector in the absence of a sample between said light source and said detector.

2. A system in accordance with claim 1, further comprising first and second filter means, wherein said first and second filter means are positioned between said light source and said first polarizer means; wherein said first and second filter means reflect radiation above about 700 nm and allow visible light to pass therethrough.

3. A system in accordance with claim 1, further comprising diffuser means for homogenizing the incident light beam from said light source.

4. A system in accordance with claim 1, further comprising a beam splitter positioned in the path of said light beam between said light source and said first polarizer means.

5. A system in accordance with claim 1, further comprising a light-tight enclosure for enclosing said system.

6. A method for verifying the calibration of a turbidimeter of the type including a light source emitting a light beam and a detector for detecting scattered light, the method comprising the steps of:

(a) positioning a first polarizer means in the path of said light beam;

(b) positioning a second polarizer means in the path of said light beam between said first polarizer means and said detector; wherein said second polarizer means is positioned such that a predetermined amount of said light beam passes therethrough to said detector in the absence of a sample between said light source and said detector.

* * * * *